(12) United States Patent
Yelin et al.

(10) Patent No.: US 9,046,419 B2
(45) Date of Patent: Jun. 2, 2015

(54) SYSTEMS AND METHODS FOR SPECTRALLY ENCODED IMAGING

(75) Inventors: Dvir Yelin, Haifa (IL); Avraham Abramov, Pardes Hana (IL)

(73) Assignee: Technion Research & Development Foundation Limited, Haifa (IL)

( * ) Notice: Subject to any disclaimer, the term of this patent is extended or adjusted under 35 U.S.C. 154(b) by 732 days.

(21) Appl. No.: 13/191,483

(22) Filed: Jul. 27, 2011

(65) Prior Publication Data

US 2012/0025099 A1 Feb. 2, 2012

Related U.S. Application Data

(60) Provisional application No. 61/368,269, filed on Jul. 28, 2010.

(51) Int. Cl.
| | |
|---|---|
| G01N 21/64 | (2006.01) |
| G01J 3/28 | (2006.01) |
| G01J 3/10 | (2006.01) |
| G01J 3/18 | (2006.01) |
| G01N 21/47 | (2006.01) |
| G02B 21/00 | (2006.01) |

(52) U.S. Cl.
CPC ............. *G01J 3/2823* (2013.01); *G01J 3/10* (2013.01); *G01J 3/1804* (2013.01); *G01N 21/474* (2013.01); *G01N 21/6456* (2013.01); *G01N 2021/4742* (2013.01); *G01N 2021/6421* (2013.01); *G01N 2021/6471* (2013.01); *G01N 2021/6484* (2013.01); *G02B 21/0076* (2013.01)

(58) Field of Classification Search
CPC .................. G01N 21/6458; G01N 2021/6421; A61B 5/0066

USPC ........................................ 250/459.1; 356/328
See application file for complete search history.

(56) References Cited

U.S. PATENT DOCUMENTS

| | | | | |
|---|---|---|---|---|
| 7,872,759 B2 * | 1/2011 | Tearney et al. | ............... | 356/479 |
| 7,889,348 B2 * | 2/2011 | Tearney et al. | ............... | 356/451 |
| 8,384,907 B2 * | 2/2013 | Tearney et al. | ............... | 356/456 |

OTHER PUBLICATIONS

"Multiple-channel spectrally encoded imaging", published Jun. 25, 2010, Optics Express, vol. 18, No. 14 to Abramov et al.*
"Spectrally-encoded color imaging", Opt Express. Aug. 17, 2009; 17(17): 15239-15247 to Kang et al.*
"Scanning fiber endoscopy with highly flexible, 1 mm catheterscopes for wide-field, full-color imaging", J. Biophoton. 3, No. 5-6, 385-407 (2010), to Lee et al.*
Kang et al. "Spectrally-Encoded Color Imaging", Optics Express, 17(17): 15239-15247, Aug. 17, 2009.
Sinclair et al. "Design, Construction, Characterization, and Application of a Hyperspectral Microarray Scanner", Applied Optics, 43(10): 2079-2088, Apr. 1, 2004.
Tearney et al. "Spectrally Encoded Confocal Microscopy", Optics Letters, 23(15): 1152-1154, Aug. 1, 1998.

* cited by examiner

*Primary Examiner* — David J Makiya
*Assistant Examiner* — Kenneth J Malkowski (57) ABSTRACT

A method of forming an image of a target that comprises illuminating a target with light, maneuvering an optical unit having at least one diffractive element in front of the target through a plurality of positions, capturing, during the maneuvering, a plurality of spectrally encoded frames each from a portion of the light that is scattered from a different of a plurality of overlapping segments along a track traversing an image plane of the target, and combining the plurality of spectrally encoded frames to form a composite multispectral image of at least a portion of said target.

25 Claims, 7 Drawing Sheets

required three optical fibers to simultaneously illuminate each point on the sample with three wavelengths from the red, green and blue parts of the spectrum.

SYSTEMS AND METHODS FOR SPECTRALLY ENCODED IMAGING

RELATED APPLICATION

This application claims the benefit of priority under 35 USC 119(e) of U.S. Provisional Patent Application No. 61/368,269 filed Jul. 28, 2010, the contents of which are incorporated herein by reference in their entirety.

FIELD AND BACKGROUND OF THE INVENTION

The present invention, in some embodiments thereof, relates to spectral imaging and, more particularly, but not exclusively, to spectral imaging using a single single-mode optical fiber.

The optical spectrum emitted from a specimen carries invaluable information on its structure, its chemical composition and physical parameters. Spectral imaging, a combination of imaging and spectroscopy, provides three dimensional data sets which contain the spectra from all the points on the imaged object. Spectral imaging has been shown useful for a wide variety of applications, including earth sciences, oceanography, homeland security, and the food industry, as well in biological and clinical applications.

Optical techniques for acquiring full spectral images often include an imaging system and spectrally dispersive element for capturing spectral information. Due to the large amount of the required information and the limited illumination intensity, a main challenge of spectral imaging is the total measurement time and the signal-to-noise ratio (SNR). In its basic form, spectral imaging is accomplished by changing colored filters in front of a camera, acquiring a series of images each with specific wavelength. Other approaches include capturing spectral cubes by spectral dispersion, using diffractive elements, such as gratings and prisms. These methods often require point-by-point scanning or line scanning, and could be combined with conventional confocal microscopes. The acquisition time in these methods depends on the scanning mechanism and the SNR which is often limited by the maximum allowable light intensity on the sample. High SNR and flexibility in selecting the spectral resolution are possible using methods which combine imaging systems with interferometers, where image acquisition is conducted by collecting interferograms of each imaged pixel and Fourier transform them into spectra.

Applications that require imaging in confined environments such as clinical endoscopy are often limited in their ability to conduct efficient spectral imaging, mainly due to limited imaging time and scanning capabilities. Spectrally encoded confocal microscopy (SECM) and spectrally encoded endoscopy (SEE), first presented in 1998 by G. J. Tearney, R. H. Webb, and B. E. Bouma, "Spectrally encoded confocal microscopy," Opt. Lett. 23 (15), 1152-1154 (1998), which is incorporated herein by reference, use a dispersive element and a lens for angularly disperse and focus a light into a transverse line on the specimen. The reflected spectrally encoded light is measured by a spectrometer for mapping the reflectance information of the specimen. A two dimensional image is formed by slowly scanning the spectral encoded line across the sample, for example, by slowly rotating the imaging probe. Since the acquired image includes only a single wavelength emitted from each point on the sample, some modifications to the system are required in order to allow effective color imaging. A recently demonstrated color-sensitive SECM system, see Dong Kyun Kang, Dvir Yelin, Brett E. Bouma, and Guillermo J. Tearney, Optics Express, Vol. 17, Issue 17, pp. 15239-15247 (2009), which is incorporated herein by reference, required three optical fibers to simultaneously illuminate each point on the sample with three wavelengths from the red, green and blue parts of the spectrum.

SUMMARY OF THE INVENTION

According to some embodiments of the present invention, there is provided a method of forming an image of a target. The method comprises illuminating a target with light, maneuvering an optical unit having at least one diffractive element in front of the target through a plurality of positions, capturing, during the maneuvering, a plurality of spectrally encoded frames each from a portion of the light which is scattered from a different of a plurality of overlapping segments along a scanning track traversing at least part of an image plane of the target, and combining the plurality of spectrally encoded frames to form a composite multispectral image of at least a part of the target.

Optionally, the capturing comprises: diffracting the portion into a single optical channel; conducting the diffracted portion; and collecting the portion using a spectral detector.

More optionally, the single optical channel is the core of a single-mode optical fiber.

More optionally, optical unit is maneuvered for example from one side to another along at least one track which is parallel to the spectral encoding direction of the plurality of spectrally encoded frames.

Optionally, the method further comprises maneuvering the single optical channel in an intrabody lumen to bring the optical unit in front of the target.

Optionally, the composite multispectral image is a full color image.

Optionally, the illuminating is performed with radiation having a wavelength selected to excite a fluorescent material in the target and the composite multispectral image is a multi wavelength fluorescence image.

Optionally, the scanning track comprises a plurality of lines parallel.

Optionally, the scanning track is non continuous.

According to some embodiments of the present invention, there is provided a method of forming a multispectral composite image of a target. The method comprises illuminating a target with light, diffracting at least a portion of the light, scattered from the target, while maneuvering at least one diffractive element in front of the target through a plurality of positions, collecting the diffracted portion to reconstruct a plurality of spectrally encoded frames having a spectral encoding direction of a plurality of overlapping segments of the target along at least one line parallel to the spectral encoding direction, and combining the plurality of spectrally encoded frames to form a composite multispectral image of at least part of the target.

According to some embodiments of the present invention, there is provided a device of imaging a target. The device comprises an optical unit having at least one diffractive element, a light source for illuminating a target with light, a single optical channel having a first end optically connected to a detector and a second end optically connected to the optical unit, an actuating unit which maneuvers the optical unit, or at least one component thereof, in a redefined pattern so as to diffract a plurality of portions of the light, scattered from a plurality of overlapping segments along a scanning track traversing at least part of an image plane of the target, and a computing unit which combines a plurality of spectrally encoded frames, formed from the plurality of portions, to generate a composite multispectral image of at least a part of the target.

Optionally, the detector is a spectrometer.

Optionally, the device is part of an endoscope or a borescope.

Optionally, the light source is an incoherent light source.

Optionally, the light source is a spatially coherent broadband source.

Optionally, the actuating unit comprises at least one motorized translation stage.

Optionally, the actuating unit comprises a micro electro mechanical systems (MEMS) mirror scanning unit.

Optionally, the actuating unit maneuvers the optical unit to diffract a plurality of portions of the light, scattered from a plurality of groups of overlapping segments along each line of a plurality of lines traversing the target; the computing unit which combines the plurality of spectrally encoded frames to generate a composite multispectral image of the target.

Optionally, the device further comprises at least one additional diffracting element between the first end of the single optical channel and the detector.

More optionally, the at least one diffracting element and the at least one additional diffracting element are optimized for the range 450-650 nm.

Optionally, the light source is a wavelength swept source and the detector being synchronized with the wavelength of the illumination of the wavelength swept source.

According to some embodiments of the present invention, there is provided a method of imaging a target using a single optical channel. The method comprises a) illuminating a target with light; b) moving at least one optical element, in front of the target, through a plurality of positions, to capture a plurality of spectrally encoded frames each of another overlapping segment along a track traversing an image plane of the target, in each the position: diffracting a portion of the light scattered from a respective the segment to form one of the plurality of spectrally encoded frames, and collecting the respective spectrally encoded frame; c) combining the plurality of spectrally encoded frames to form a composite multispectral image of the track.

Optionally, the method further comprises d) combining the composite multispectral image with other of a plurality of composite multispectral images to form an image of the target.

Optionally, the d) combining comprises d) iteratively repeating the b) and c); wherein in each iteration the at least one optical element is moved to capture a respective the plurality of spectrally encoded frames along an additional track traversing the target; and wherein the track and the additional track are parallel to one another.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a nonvolatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to spectral imaging and, more particularly, but not exclusively, to spectral imaging using a single single-mode optical fiber.

According to some embodiments of the present invention, there are provided methods and devices of forming a multispectral composite image of a target by reconstructing spectrally encoded frames from light scattered from overlapping segments of the target along one or more tracks (lines) which are parallel to the spectral encoding direction of the spectrally encoded frames. Optionally, the multispectral composite image is a full color image or a multi wavelength fluorescence image of the target.

According to some embodiments of the present invention, the method(s) are performed by illuminating a target with light, optionally incoherent, maneuvering an optical unit having one or more diffractive elements in front of the target through a plurality of positions, and capturing, during the maneuvering, spectrally encoded frames. Each frame is generated from a portion of the light that is scattered from one of a plurality of overlapping segments along a track, such as a line traversing the target along axis X or any other axis, along a curved line traversing the target, along a circular track and/or any other continuous or noncontinuous scanning track. This allows combining the spectrally encoded frames to form a composite multispectral image of at least a portion of the target.

According to some embodiments of the present invention, the device(s) include an optical unit having one or more diffractive elements, such as gratings, a light source for illuminating a target with light, and a single optical channel having a first end optically connected to a detector and a second end optically connected to the optical unit. Optionally, the light source is connected to a light waveguide for conducting toward the target. In such an embodiment, the device may function as a device for inspecting narrow lumens, such as intrabody lumens, for example as an endoscope or a borescope. The device further includes an actuating unit, such as one or more motorized translation stages, which maneuvers the optical unit, or any component thereof, in a predefined pattern so as to diffract a plurality of portions of light that is scattered from a plurality of overlapping segments along any of one or more tracks, such as lines traversing the target and a computing unit which combines a plurality of spectrally encoded frames, formed from the plurality of portions, to generate a composite multispectral image of at least a portion of the target.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1A:
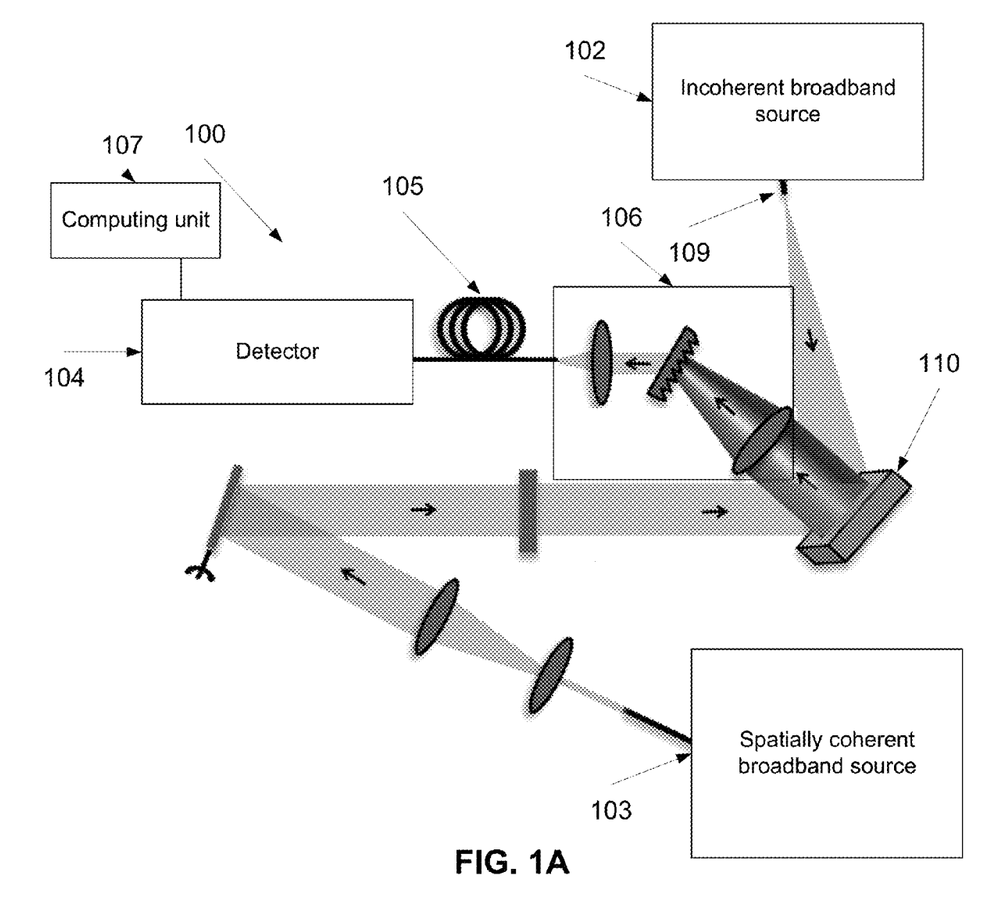
FIG. 1A is a schematic illustration of a multi wavelength imaging device of capturing a multispectral composite image of a target using a single optical channel, according to some embodiments of the present invention.

Reference is now made to FIG. 1A, which is a schematic illustration of a multi wavelength imaging device 100 of capturing a multispectral image of a target 110 using a single optical channel, such as an optical fiber designed to carry only a single ray of light (mode), for example a single-mode optical fiber, according to some embodiments of the present invention. As used herein a multispectral image may be a full color image, a multi wavelength fluorescence image, and/or the like.

The imaging device 100, which is optionally a spectrally encoded endoscopy device for spectrally-encoded imaging, includes a radiation source, such as an incoherent light source 102, for example an incoherent light source which transmits, optionally via a light waveguide 109, such as an optical fiber, incoherent light. For example, the incoherent light source is a Halogen lamp (i.e. 150 W). Additionally or alternatively, the imaging device 100 includes a spatially coherent broadband source 103, such as a supercontinuum source, for instance SC450 of Fianium™ Inc. Additionally or alternatively, the imaging device 100 includes a wavelength-swept source. In such an embodiment, the detector which is described below may be synchronized with the illumination wavelength.

The imaging device 100 further includes an optical waveguide 105, optionally with a single light channel, such as a single-mode optical fiber, for example S405-HP fiber of Nufern™. The light waveguide 105 has an optical unit 106 with one or more diffractive elements connected to its distal end. The width of the optical unit 106 is optionally about the same as the width of the single light channel.

For example, the optical unit 106 includes an imaging lens, such as an imaging lens having 25 mm focal length and 25 mm diameter and a diffractive element, such as a 1200 lines/mm transmission grating of Wasatch Photonics™. Optionally, an achromatic lens, such as a 25 mm focal length lens, is used to focus light diffracted by the one or more diffractive elements into the single light channel 105, for example the core of a single-mode optical fiber. Optionally, the optical unit 106 is defined with a spatial interval $\delta x$ along a wavelength axis at the center field of view is then related to a corresponding wavelength interval $\delta \lambda$ according to $\delta x = G f \cdot \delta \lambda / \cos \theta_0$ where G denotes the grating groove density, f denotes the focal length of the imaging lens and $\theta_0$ denotes the Littrow's angle.

The imaging device 100 further includes a detector 104, such as a spectrometer detector array, which is connected to the distal end of the light waveguide 105. Optionally, the detector 104 is a spectrometer which comprised of a diffractive element, for example a grating, such as 1800 lines/mm transmission diffraction grating of Wasatch Photonics™, a lens, such as Nikon™ AFC, 50 mm focal length lens, and a high sensitivity back-illuminated electron multiplication charged coupled device (EMCCD) camera, such as DU970N-BV of Andor™.

Optionally, when the illumination source is a wavelength-swept source, the detector 104 is a photodiode or a photomultiplier tube which is synchronized with the sweep frequency of the optional wavelength swept source.

Optionally, an objective lens, such as Leica™, Achro 0.1 NA, is connected at the proximal end of the single light waveguide 105 to collimate light passing therethrough and directing it into the detector 104.

Optionally, the diffractive element of the optical unit 106 and/or the diffractive element of the spectrometer are optimized for the range 450-650 nm, with 550 nm at Littrow's angles. Light diffracted from the optical unit 106 is translated by the detector 104 to a spectral encoded frame and/or line. A spectrally encoded frame spectrally encodes reflectance across a segment within the target where each wavelength encodes reflectance across a different portion of the segment. For example, the segment may be rectangular, square, triangular, and/or circular.

The imaging device 100 further includes an actuating unit for maneuvering the optical unit 106, for example the one or more diffractive elements thereof, the imaging lens, and/or a mirror that direct light reflected from the target 110 toward the imaging lens, through a plurality of different positions. In each position, a spectral encoded frame of a segment of the target 110 is captured, for example by a computing unit 107 that is connected to the detector 104, such as a workstation, a desktop, a laptop, and/or a tablet. The maneuvering of the optical unit 106 is performed so as to capture multi wavelength data from a plurality of overlapping segments along a scanning track traversing an image plane of the target 110, for example a line, for instance as further described below.

Figure 1B:
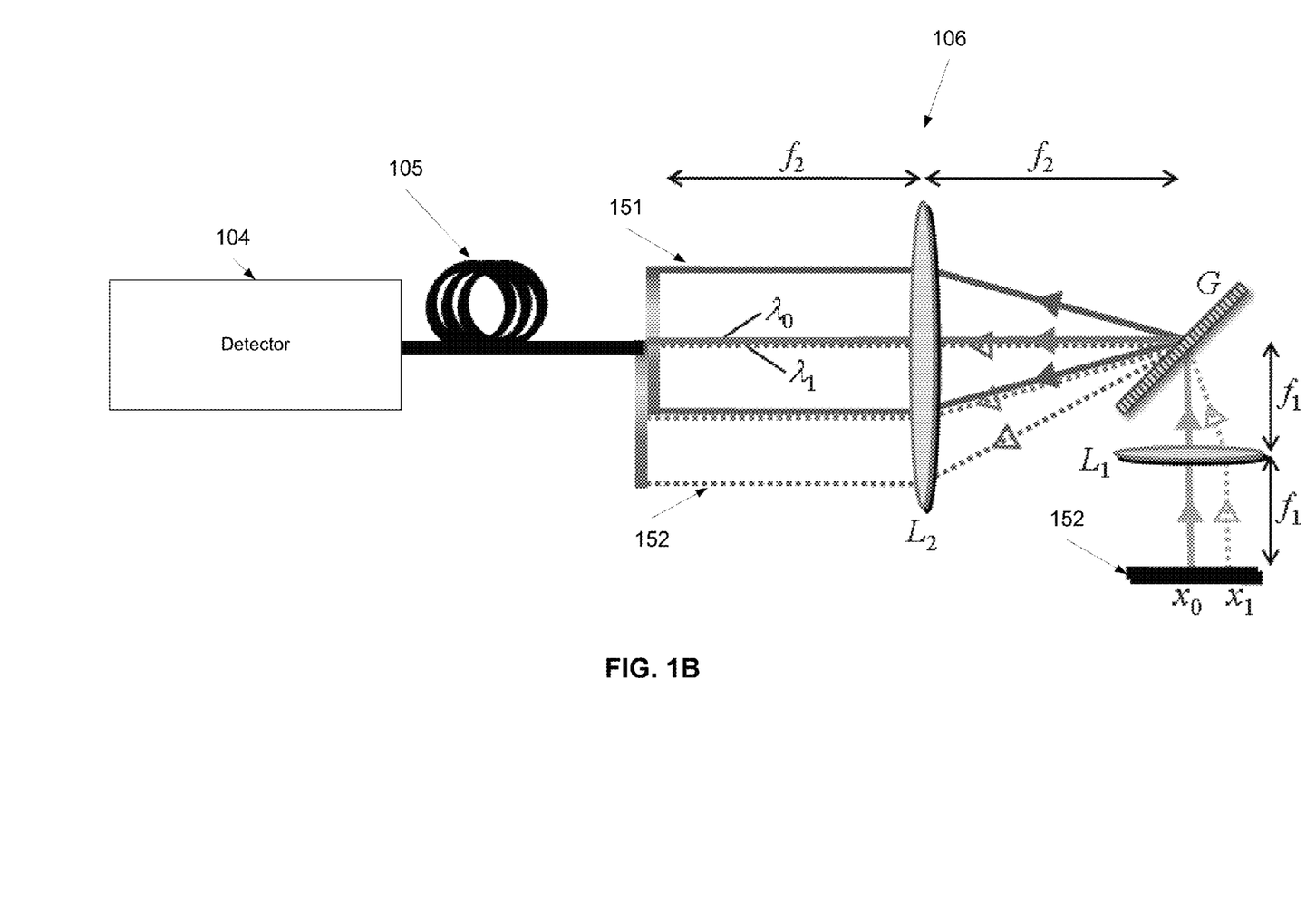
FIG. 1B is a schematic illustration of light scattered from the target and diffracted by the optical unit of the imaging device, according to some embodiments of the present invention.

For instance, reference is also made to FIG. 1B, which is a schematic illustration of light scattered from the target and diffracted to the optical unit of the imaging device 100, according to some embodiments of the present invention. The continuous color lines depict light scattered from a certain segment of an exemplary target 152 and diffracted by a diffractive element of an optical unit, as described above and the dotted color lines depicts light scattered from an overlapping segment of the exemplary target 152 and diffracted by the diffractive element. In use, the diffractive element is maneuvered, for example moved or tilted, to capture spectral encoded frames of both the certain segment and the overlapping segment, optionally sequentially, so as to acquire multispectral data pertaining to the target.

Optionally, the optical unit 106 is maneuvered to capture multi wavelength data from a plurality of overlapping segments along each of a plurality of parallel lines traversing an image plane of the target 110. As outlined above, the optical unit 106 may be maneuvered to capture the multi wavelength data according to other scanning patterns which are set so that at each a desired number of the wavelengths are captured from each pixel in the image plane of the target.

Optionally, motorized translation stages are used for the maneuvering. Optionally, a micro electro mechanical systems (MEMS) mirror scanning unit is used for maneuvering a scanning beam. In use, the actuating unit actuates the optical unit 106, or one or more components thereof, in a predefined scanning pattern so as to diffract a plurality of portions of light scattered from a plurality of overlapping segments of track(s), such as one or more traversing lines, across an image plane of the target 110. Optionally, the predefined scanning pattern is set to acquire a plurality of portions of incoherent light from a two dimensional, optionally quadric or a square, image plane. In such an embodiment, for example, a first motorized translation stage maneuvers the optical unit 106 on a first axis to scan overlapping segments in any of one or more plurality of axes which are parallel to the first axis and a second motorized translation stage maneuvers the optical unit 106 on a second axis, which is perpendicular to the first axis, to maneuver the optical unit 106 between the plurality of axes. In such an embodiment, the spectral encoded frames image a two dimensional matrix that image the image plane of the target wherein frames along each line of the matrix image overlapping segments.

During the scan, the computing unit 107 acquires the plurality of spectral encoded frames from the detector 101 and combines them to generate a multispectral composite image or a multi wavelength fluorescence image of the target 110, for example as described below.

Figure 2:
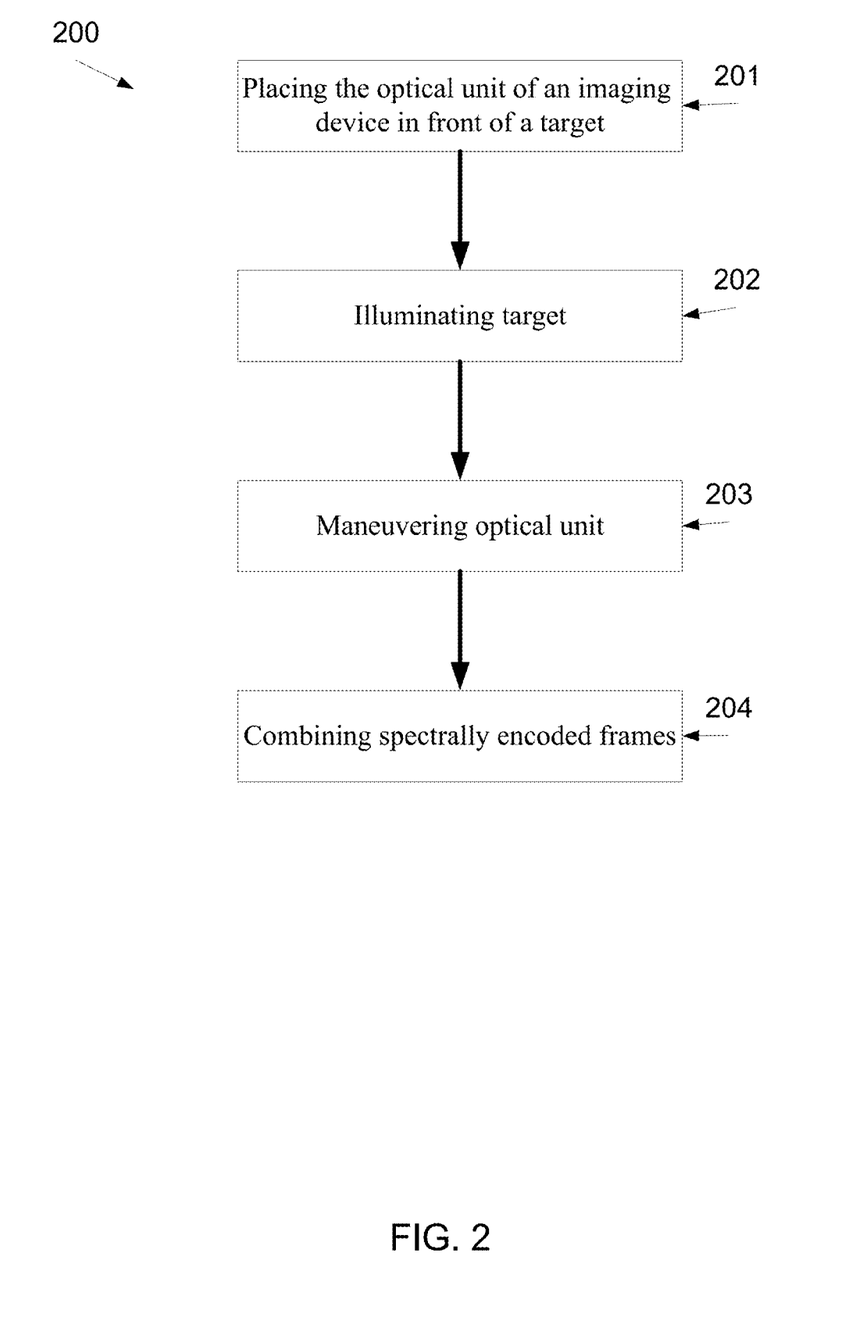
FIG. 2 is a flowchart of a method for multispectral imaging of a target by combining a plurality of spectral encoded frames captured via a single optical channel, according to some embodiments of the present invention.

Reference is now also made to FIG. 2, which is a flowchart 200 of a method for multispectral imaging of a target by combining a plurality of spectral encoded frames captured via a single optical channel, according to some embodiments of the present invention.

First, as shown at 201, an imaging device, such as 101, is provided so that the optical unit 106 is brought in front of a target, for example as depicted in FIGS. 1A and 1B. The proximal end of the single optical channel, which is optionally a diffractive element mounted at the tip of a single-mode optical fiber, may be threaded in a catheter of an endoscope or a borescope. The endoscope or a borescope can now be used to guide the optical unit 106 through intrabody lumens. As the waveguide is optionally a single channel waveguide, such as a single-mode optical fiber, the optical unit 106 may be threaded via narrow lumens, such as narrow vascular structures.

Than, as shown at 202, a target is illuminated with light, optionally incoherent, for example using one of the aforementioned illumination sources. Optionally, if the process 200 is used for generating a multi wavelength fluorescence image, the illumination radiation is excitation radiation for exciting fluorescent material in or on the target.

Optionally, radiation from the illumination source is conducted toward the target on a light waveguide, such as an optical fiber.

Now, as shown at 203, during the illumination, the optical unit at the tip of the single-mode optical fiber is maneuvered in front of the target through a plurality of positions to acquire one or more groups of spectrally encoded frames of overlapping segments of the target along a scanning track, for example along one or more transverse lines. During the maneuvering, each spectrally encoded frame is captured from another portion of the light that is scattered from the segments of the target. The maneuvering is performed to form a scanning pattern, for example from one side to another along a track which is parallel to the spectral encoding direction (X-axis), and then similarly in other parallel tracks which are parallel to the spectral encoding direction. Alternatively, the scanning pattern is along a track that is perpendicular to the spectral encoding direction (Y-axis) and then similarly in other parallel tracks which are perpendicular to the spectral encoding direction. Alternatively, the maneuvering is performed in any other pattern that allows acquiring a desired set of wavelengths from each point of the target with minimal repetitions to maintain scanning efficiency.

Now, as shown at 204, the spectrally encoded frames are combined to form a multispectral composite image of the target, such as a full color image and/or a multi wavelength fluorescence image. Composite spectral data, such as color, of each pixel in the multispectral composite image may be calculated by combining the respective pixels from respective frames. For example, an RGB composite image is formed by summarizing the respective pixel values into RGB vectors. Optionally, white regions in the composite image are used for white balance calibration.

As described above each spectrally encoded frame spectrally encodes reflectance across a track, such as a line, traversing the target where each wavelength encodes reflectance across a different portion of the track, for example the transverse line. In order to image every pixel along the track (i.e. transverse lines), a plurality of spectrally encoded frames which image portions of the scanning track in an overlapping manner are captured and combined. For example, a plurality of spectrally encoded frames which image a plurality of overlapping segments along a certain scanning track in an image plane of the target are combined. Optionally, the scanning is performed so that each segment of the target is imaged by three spectrally encoded frames and in each frame by a different wavelength, for example respectively at the blue, green and red parts of the spectrally encoded frames. Optionally, the scanning is performed so that each segment of the target is imaged by any number of spectrally encoded frames and in each frame by a different wavelength so as to extract various spectral data.

Figure 3A:
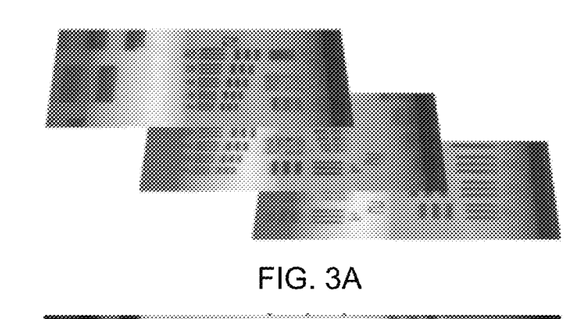
FIGS. 3A-3D are images of exemplary laterally translated spectrally encoded frames, respective multispectral composite images, and a CIE-XY diagram, according to some embodiments of the present invention.
Figure 3B:
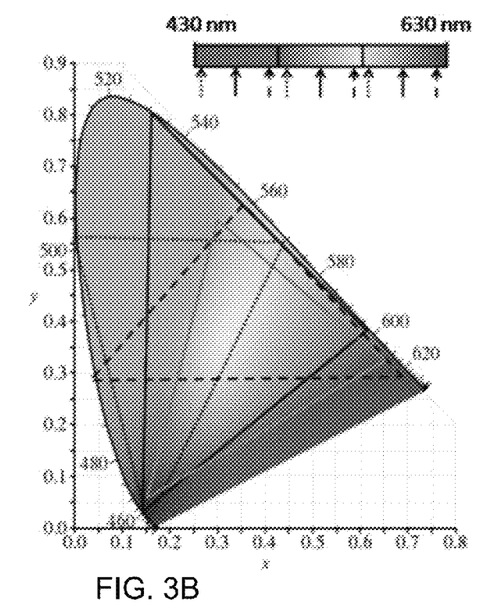
Figure 3C:
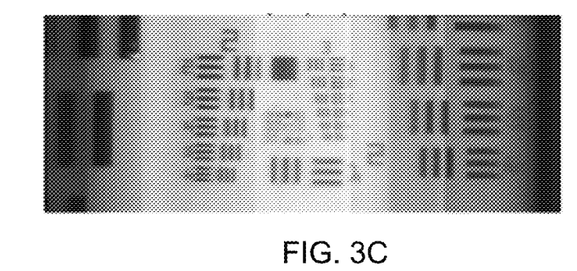
Figure 3D:
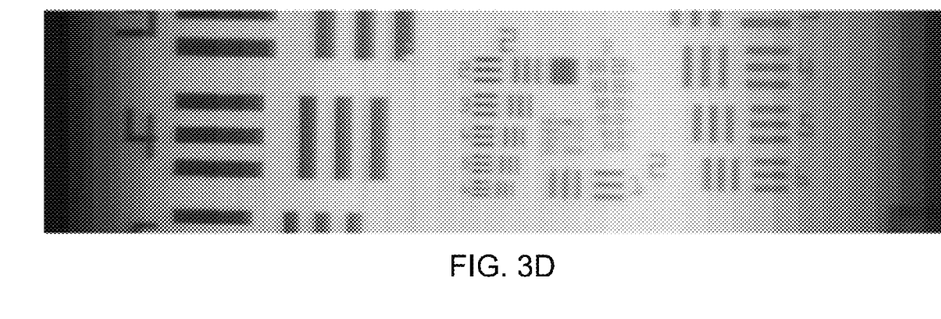

Reference is now also made to FIGS. 3A-3D. FIG. 3A depicts three exemplary laterally translated spectrally encoded, color-coded, frames of an exemplary black-on-white printed resolution target. FIG. 3B depicts an international commission on illumination (CIE)-XY diagram with three color gamut triangles corresponding to different spatial lines in the target, marked by dashed, solid, and dotted lines where color gamut of the standard red green blue (sRGB) color base is marked by a gray triangle. FIG. 3C depicts a color composite image of the target, assembled from the three spectral encoded frames of FIG. 3A which were gradually translated in a wavelength axis. FIG. 3D depicts a color composite image of the target, assembled from thirty overlapping spectrally encoded raw frames which were gradually translated in a wavelength axis. In the example depicted in FIG. 3D, the thirty overlapping spectrally encoded raw frames where acquired, as described above, by shifting the optical unit 106 along the spectral encoding direction (X-axis) so that a deviation of 0.48 mm separate between the frames, corresponding to approximately 14 nm wavelength shifts for the respective imaged segment. Evidently, additional scanning in the spectral encoding direction would increase the total field of view, and consequently the region at which accurate color could be obtained. The more frames are captured per traverse line, for example by decreasing the lateral steps between acquisitions, the higher is the spectral resolution of the multispectral composite image, for example as high as the spectral resolution $\delta\lambda$ of the encoded imaging channel. As a result, the data collected from each segment of the target may include its perceived color and optionally a full spectrum of the emitted/scattered light. This is true also if the scanning track does not include straight lines, but rather curved lines, circular patterns, and/or the like.

Figure 4A:
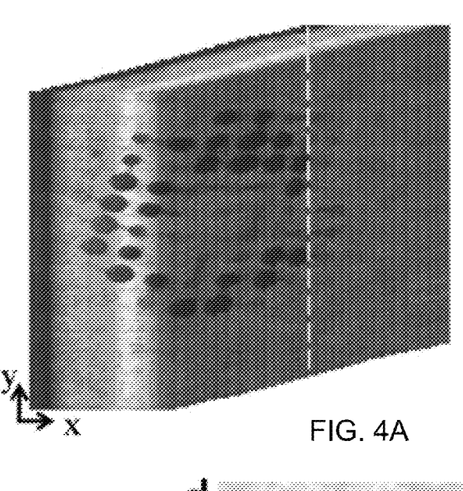
FIGS. 4A-4E are image which exemplify spectral imaging using the imaging device depicted in FIG. 1A, according to some embodiments of the present invention.

Reference is now made to FIGS. 4A-4E which exemplify spectral imaging using the imaging device depicted in FIG. 1A, according to some embodiments of the present invention. FIG. 4A depicts a three-dimensional raw data cube contained 1600×500×N monochromatic pixels (16 bit), where N=30 denotes the total number of laterally-shifted frames. This three-dimensional raw data cube has been acquired by spectral encoding frames of segments of a colored pattern printed on white paper using commercial color inkjet printer and depicted in FIG. 4E.

Figure 4B:
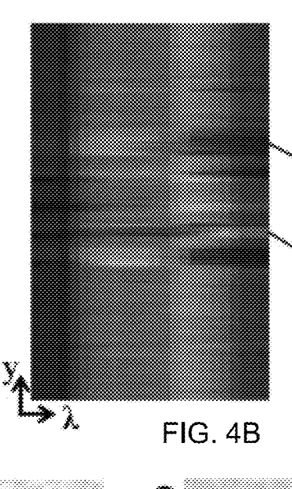
Figure 4C:
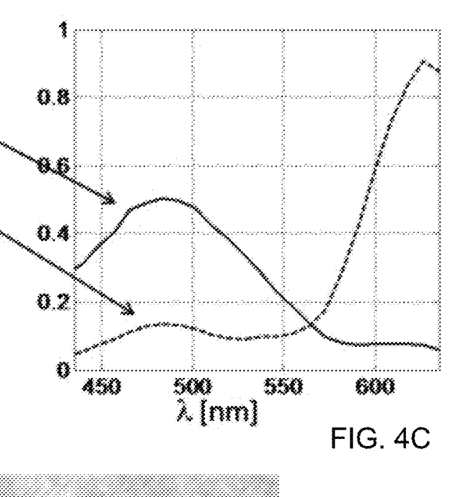
Figure 4D:
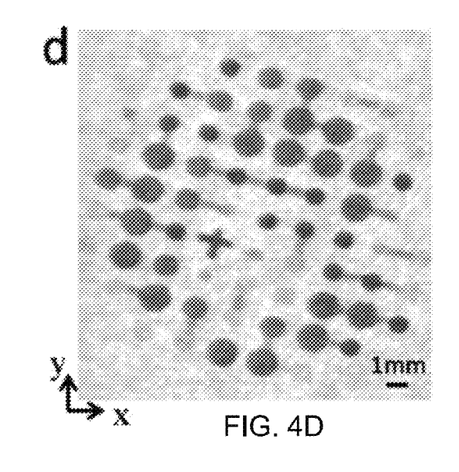
Figure 4E:
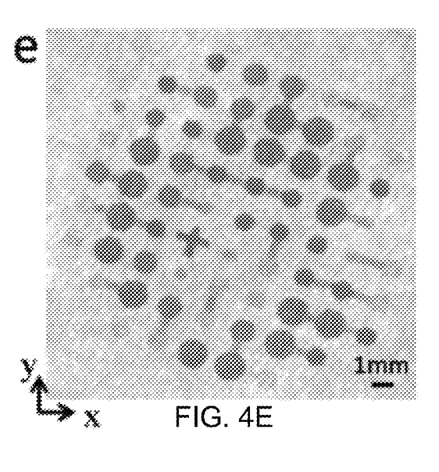

FIG. 4B depicts a single y-$\lambda$ plane in the data set, whose location in the x-axis is marked by a dashed line in FIG. 4A, contained the full spectra of each point across that line. Two selected reflection spectra are shown in FIG. 4C, corresponding to a single blue spot (solid curve) and a single red spot (dashed curve) on the image. For obtaining the actual color composite image of the target, the data is collapsed onto a 1600×500×3 matrix by calculating the projection of the acquired spectra onto the three RGB vectors, for example see FIG. 3D.

As described above, the illumination source may be a spatially coherent light source. Using such an illumination source provides the imaging process with better exposure time and higher signal to noise ratio (SNR). To demonstrate spectral imaging using coherent illumination, a beam from a supercontinuum source, SC-400-4 of Fianium™, was focused onto an imaged line using an optical unit containing a scanning mirror, a lens and a cylindrical lens. The total power illuminating the sample was approximately 50 mW. A full scan of the mirror was accomplished during the acquisition of each line, resulted with nearly 80% reduction of speckle noise in relation to a similar experiment with incoherent illumination.

Reference is now made to a signal to noise ratio (SNR) analysis. Optionally, when scanning using the imaging device 100 for capturing spectrally encoded frames.

The signal (in electrons) measured for each resolvable element (x, y, $\lambda$) is equal to $Q_e r(I_{max}s/hv)t$, where $Q_e$ denotes the detector quantum efficiency, r denotes sample reflectivity, $I_{max}$ denotes the maximum permissible exposure (MPE) in units of W/cm$^2$, s denotes the area of a single spatial resolvable element, v denotes the optical frequency, and t denotes the exposure time of a single resolvable element. When both the illumination and collection channels are spectrally encoded, each pixel in a single N×N pixel frame is sequentially illuminated by a single wavelength only, while the detection of the light reflected from that pixel is performed on a single detector during the entire exposure time given by Equation 1:

$$t = \frac{T}{N}\frac{1}{N+M-1}$$

where T denotes the total imaging time and M denotes the number of (spectral) resolvable elements in the wavelength axis. Assuming that dark current is the dominant noise source (neglecting shot noise and read noise) the SNR is given by (N,M>>1):

Equation 2:

$$SNR_{SESI} = \frac{Q_e r \frac{I_{max}s}{hv}\frac{T}{N}\frac{1}{N+M}}{\sqrt{D\frac{T}{N}\frac{1}{N+M}}} = \frac{Q_e r I_{max}s\sqrt{T}}{hv\sqrt{D}}\sqrt{\frac{1}{N(N+M)}}, \quad (1)$$

where D denotes the dark current in electrons per second per pixel.

In comparison, when scanning the sample point-by-point with a tightly focused laser beam and measuring its spectrum to obtain a spectral image, the signal measured for each resolvable element (x, y, $\lambda$) is given by $$Q_e \frac{r(I_{max}s/hv)}{M}t_{p-p},$$

where $t_{p-p}=T/N^2$ denotes the exposure time for a single pixel in point-by-point scanning. Assuming that dark current is the dominant noise source, the SNR for point-by-point spectral imaging is given by:

Equation 3:

$$SNR_{p-p} = \frac{Q_e \frac{r(I_{max}s/hv)}{M}\frac{T}{N^2}}{\sqrt{D\frac{T}{N^2}}} = \frac{Q_e r I_{max}s\sqrt{T}}{hv\sqrt{D}}\frac{1}{MN}.$$

When the sample is scanned by an entire focused line and the spectral cube is acquired by a two-dimensional CCD, see M. B. Sinclair, J. A. Timlin, D. M. Haaland, and M. Werner-Washburne, "Design, construction, characterization, and application of a hyperspectral microarray scanner," Appl. Opt. 43, 2079-2088 (2004), which is incorporated herein by reference. Each spatial pixel in the image could still be illuminated by irradiance $I_{max}$, however the total exposure time would now be N-times longer than that of point scanning, thus the SNR for line-by-line spectral imaging is given by:

Equation 4:

$$SNR_{l-l} = \frac{Q_e \frac{r(I_{max}s/h\nu)}{M} \frac{T}{N}}{\sqrt{D\frac{T}{N}}} = \frac{Q_e r I_{max} s \sqrt{T}}{h\nu \sqrt{D}} \frac{1}{M\sqrt{N}}.$$

Assuming, for brevity, that the number of resolvable wavelengths is equal to the number of spatial resolvable elements (M=N) the following is obtained:

Equation 5:

$$SNR_{SESI} : SNR_{l-l} : SNR_{p-p} = \frac{N}{\sqrt{2}} : \sqrt{N} : 1,$$

implying that the imaging devices of the present application have an SNR advantage over line-by-line and point-by-point scanning by a factor which equals $\sqrt{N/2}$ and $N/\sqrt{2}$, respectively. Note that the additional field of view at the edges of the SESI frame, which do not contain full spectral information, where not considered in the derivation of Equations (2) and (5).

The large advantage in SNR of the present imaging devices over other spatial scanning techniques, as reflected in Equation 5, holds only when the illumination and the collection channels are both spectrally encoded. In specific configurations where one of the channels is not spectrally encoded, for example when using broadband wide field illumination as presented in the above experimental demonstration, the signal, and consequently the SNR, would be M-times smaller than that used in Equation 2.

It is expected that during the life of a patent maturing from this application many relevant devices and methods will be developed and the scope of the term optical units, diffractive elements, computing units, and spectrometers is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions; illustrate some embodiments of the invention in a non limiting fashion.

Figures 5A, 5B, 5C:
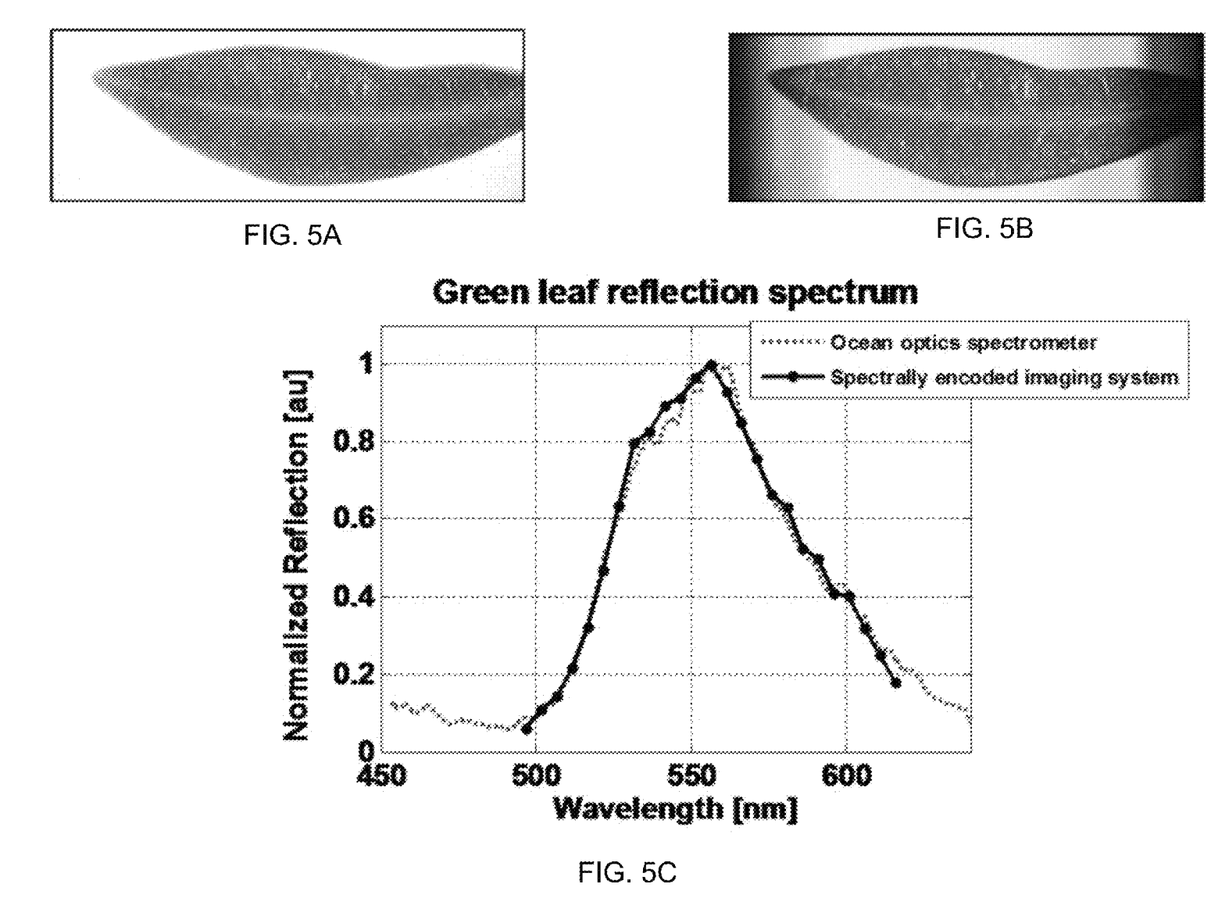
FIGS. 5A-5C are images of an exemplary green leaf, a composite color image of the same leaf, and a graph that depicts a comparison between the measured reflectance spectrum of the leaf at a single point using the imaging device and the measured reflectance spectrum at that point by a commercial spectrometer, according to some embodiments of the present invention.

Reference is now made to FIGS. 5A-5C. FIG. 5A is an image of an exemplary green leaf and to FIG. 5B is a composite color image constructed from 65 spectrally encoded frames, captured using the device depicted in FIG. 1A, imaging segments of the green leaf, using a scanning pattern of 50 ms exposure time per spectrally encoded frame. After each spectrally encoded frame is captured, the optical unit is shifted to capture another spectrally encoded frame of another segment in steps of 0.2 mm along the wavelength axis of the, corresponding to a spectral resolution of approximately 6.5 nm. A comparison between the measured reflectance spectrum of the leaf at a single point using the imaging device and the measured reflectance spectrum at that point by a commercial spectrometer (Ocean Optics™ usb4000 inc) is demonstrated in FIG. 5C by a solid curve and a dotted curve, respectively. These curves show an overlap between 500 nanometer (nm) and 620 nm.

Figure 6A:
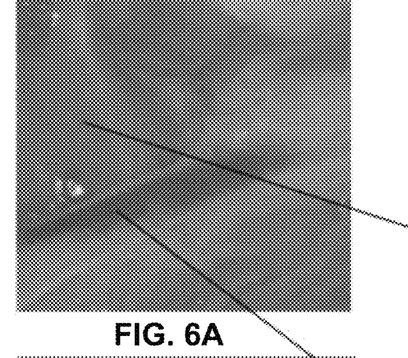
FIGS. 6A-6E are images of an exemplary tissue, a composite color image of the same tissue, and respective spectra curves, according to some embodiments of the present invention.
Figure 6B:
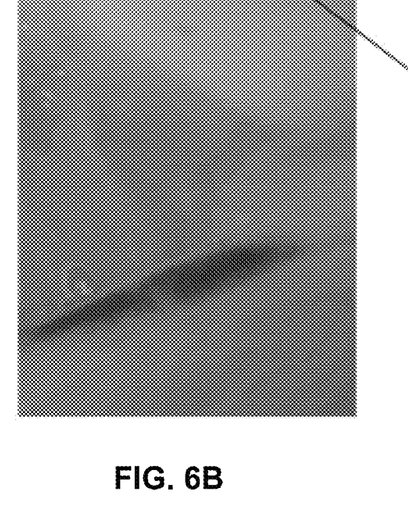
Figure 6C:
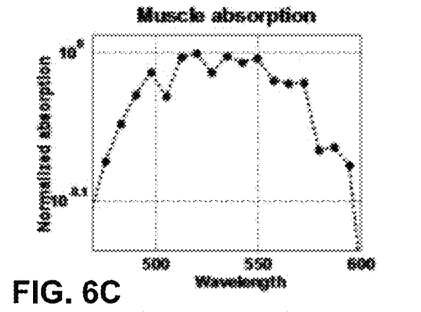
Figure 6D:
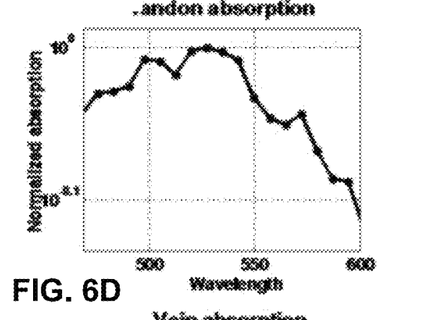
Figure 6E:
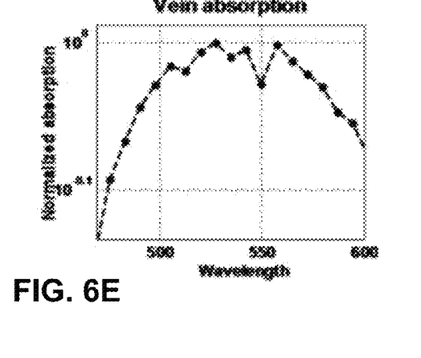

Reference is now made to FIGS. 6A-6E. FIG. 6A is an image of an exemplary living cells specimen, a fresh chicken tissue and to FIG. 6B which is a composite color image constructed from spectrally encoded frames, captured using the device depicted in FIG. 1A, imaging segments of the living cells specimen. FIGS. 6C-6E depicts spectra curves corresponding to the locations in the image, marked by arrows. These spectra curves show the spectra absorption of a muscle tissue, a tendon, and a vein, respectively.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of forming an image of a target, comprising:
   illuminating a target with light;
   maneuvering an optical unit having at least one diffractive element in front of said target through a plurality of positions;
   capturing, during said maneuvering, a plurality of spectrally encoded frames each from light in a plurality of different wavelengths, each one of said plurality of different wavelengths is scattered from a different segment of a plurality of parallel segments along a scanning track traversing at least part of an image plane of said target; and
   combining pixel values of said plurality of spectrally encoded frames imaging each one of said plurality of segments by at least two of said plurality of different wavelengths to form a composite multispectral image of at least a part of said target.

2. The method of claim 1, wherein said capturing comprises:
   diffracting said plurality of different wavelengths into a single optical channel;
   conducting said plurality of diffracted wavelengths; and
   collecting said portion using a spectral detector.

3. The method of claim 2, wherein said single optical channel is the core of a single-mode optical fiber.

4. The method of claim 2, wherein optical unit is maneuvered from one side to another along at least one track which is parallel to the spectral encoding direction of said plurality of spectrally encoded frames.

5. The method of claim 1, further comprising maneuvering said single optical channel in an intrabody lumen to bring said optical unit in front of said target.

6. The method of claim 1, wherein said composite multispectral image is a full color image.

7. The method of claim 1, wherein said illuminating is performed with radiation having a wavelength selected to excite a fluorescent material in said target and said composite multispectral image is a multi wavelength fluorescence image.

8. A non-transitory computer readable medium comprising computer executable instructions adapted to perform the method of claim 1.

9. The method of claim 1, wherein said scanning track comprises a plurality of lines parallel.

10. The method of claim 1, wherein said scanning track is non continuous.

11. A method of forming a multispectral composite image of a target, comprising
    illuminating a target with light;
    diffracting at least a portion of said light, scattered from said target, while maneuvering at least one diffractive element in front of said target through a plurality of positions;
    collecting said diffracted portion to reconstruct a plurality of spectrally encoded frames having a spectral encoding direction of a plurality of parallel segments of said target along at least one line parallel to said spectral encoding direction, each one of said plurality of spectrally encoded frames is from a plurality of different wavelengths, each one of said plurality of different wavelengths is scattered from a different segment of said plurality of segments; and
    combining pixel values of said plurality of spectrally encoded frames imaging each one of said plurality of segments by at least two of said plurality of different wavelengths to form a composite multispectral image of at least part of said target.

12. A device of imaging a target, comprising:
    an optical unit having at least one diffractive element;
    alight source for illuminating a target with light;
    a single optical channel having a first end optically connected to a detector and a second end optically connected to said optical unit;
    an actuating unit which maneuvers said optical unit, or at least one component thereof, in a predefined pattern so as to diffract a plurality of portions of said light, scattered from a plurality of parallel segments along a scanning track traversing at least part of an image plane of said target; and
    a computing unit which combines a plurality of spectrally encoded frames, each one of said plurality of spectrally encoded frames is from said plurality of portions wherein each one of said plurality of portions having one of a plurality of different wavelengths, to generate a composite multispectral image of at least a part of said target by combining pixel values of said plurality of spectrally encoded frames.

13. The device of claim 12, wherein said detector is a spectrometer.

14. The device of claim 12, wherein said device is part of an endoscope or a borescope.

15. The device of claim 12, wherein said light source is an incoherent light source.

16. The device of claim 12, wherein said light source is a spatially coherent broadband source.

17. The device of claim 12, wherein said actuating unit comprises at least one motorized translation stage.

18. The device of claim 12, wherein said actuating unit comprises a micro electro mechanical systems (MEMS) mirror scanning unit.

19. The device of claim 12, wherein said actuating unit maneuvers said optical unit to diffract a plurality of portions of said light, scattered from a plurality of groups of parallel segments along each line of a plurality of lines traversing said target; said computing unit which combines said plurality of spectrally encoded frames to generate a composite multispectral image of said target.

20. The device of claim 12, further comprising at least one additional diffracting element between said first end of said single optical channel and said detector.

21. The device of claim 20, wherein said at least one diffracting element and said at least one additional diffracting element are optimized for the range 450- 650 nm.

22. The device of claim 12, wherein said light source is a wavelength swept source and said detector being synchronized with said wavelength of the illumination of said wavelength swept source.

23. A method of imaging a target using a single optical channel, comprising:
   a) illuminating a target with light;
   b) moving at least one optical element, in front of said target, through a plurality of positions, to capture a plurality of spectrally encoded frames each from light in a plurality of different wavelengths, each one of said plurality of different wavelengths is scattered from another segment of a plurality of parallel segments along a track traversing an image plane of said target, in each said position:
      diffracting a portion of said light scattered from a respective said segment to form one of said plurality of spectrally encoded frames, and
      collecting said respective spectrally encoded frame;
   c) combining pixel values of said plurality of spectrally encoded frames to form a composite multispectral image imageing one of said plurality of segments of said track by at least two of said plurality of different wavelengths.

24. The method of claim 23, further comprising d) combining said composite multispectral image with other of a plurality of composite multispectral images to form an image of said target.

25. The method of claim 24, wherein said d) combining comprises d) iteratively repeating said b) and c);
   wherein in each iteration said at least one optical element is moved to capture a respective said plurality of spectrally encoded frames along an additional track traversing said target; and
   wherein said track and said additional track are parallel to one another.

* * * * *